(12) United States Patent
Tochinai et al.

(10) Patent No.: US 12,398,048 B2
(45) Date of Patent: Aug. 26, 2025

(54) METHOD FOR PREDICTING PARTICULATE BREAKTHROUGH TIME FOR NON-REGENERATIVE ION EXCHANGE RESIN DEVICE AND METHOD FOR MANAGING NON-REGENERATIVE ION EXCHANGE RESIN DEVICE

(71) Applicant: KURITA WATER INDUSTRIES LTD., Tokyo (JP)

(72) Inventors: Masahito Tochinai, Tokyo (JP); Yoichi Miyazaki, Tokyo (JP)

(73) Assignee: KURITA WATER INDUSTRIES LTD., Tokyo (JP)

( * ) Notice: Subject to any disclaimer, the term of this patent is extended or adjusted under 35 U.S.C. 154(b) by 912 days.

(21) Appl. No.: 17/610,685

(22) PCT Filed: Feb. 25, 2020

(86) PCT No.: PCT/JP2020/007426
§ 371 (c)(1),
(2) Date: Nov. 11, 2021

(87) PCT Pub. No.: WO2021/029094
PCT Pub. Date: Feb. 18, 2021

(65) Prior Publication Data
US 2022/0212953 A1 Jul. 7, 2022

(30) Foreign Application Priority Data
Aug. 15, 2019 (JP) .................. 2019-149121

(51) Int. Cl.
*C02F 1/08* (2023.01)
*C02F 1/00* (2023.01)
(Continued)

(52) U.S. Cl.
CPC ............... *C02F 1/008* (2013.01); *C02F 1/42* (2013.01); *G01N 15/0826* (2013.01); *C02F 2209/001* (2013.01); *C02F 2209/44* (2013.01)

(58) Field of Classification Search
CPC ........ C02F 1/008; C02F 1/42; C02F 2209/00; C02F 2209/44; C02F 1/32; C02F 1/441;
(Continued)

(56) References Cited

FOREIGN PATENT DOCUMENTS

| JP | H11101761 | 4/1999 |
|---|---|---|
| JP | 2012154634 | 8/2012 |

(Continued)

OTHER PUBLICATIONS

Google English Translation of JP 2012154634 A, Aug. 2012.*
(Continued)

*Primary Examiner* — Thuan D Dang
(74) *Attorney, Agent, or Firm* — JCIPRNET

(57) ABSTRACT

Provided is a method for predicting particulate breakthrough time for a non-regenerative ion exchange resin device, in which a portion of water to be treated by a non-regenerative ion exchange resin device passes through each of the following that are disposed in parallel with the non-regenerative ion exchange resin device: a first path that includes a first particle counter; a second path that includes a first compact resin column, a second particle counter, a flow rate regulating valve, and a first flow meter; and a third path that includes a second compact resin column, a third particle counter, a flow rate regulating valve, and a second flow meter.

9 Claims, 4 Drawing Sheets

(51) Int. Cl.
*C02F 1/42* (2023.01)
*G01N 15/08* (2006.01)
(58) Field of Classification Search
CPC .. C02F 1/442; C02F 2103/04; C02F 2209/10; C02F 2209/40; G01N 15/0826; G01N 30/44; G01N 30/00; G01N 30/02; G01N 30/64; G01N 30/88
See application file for complete search history.

(56) References Cited

FOREIGN PATENT DOCUMENTS

| | | | |
|---|---|---|---|
| JP | 2012154634 A * | 8/2012 | |
| JP | 2019076844 | 5/2019 | |
| TW | 201801789 | 1/2018 | |
| WO | 2015050125 | 4/2015 | |
| WO | 2017164361 | 9/2017 | |
| WO | WO-2017164361 A1 * | 9/2017 | ........... B01D 61/145 |

OTHER PUBLICATIONS

Google English Translation of WO 2017/164361 A1, Sep. 2017.*
"International Search Report (Form PCT/ISA/210) of PCT/JP2020/007426," mailed on May 26, 2020, with English translation thereof, pp. 1-4.
"Office Action of Taiwan Counterpart Application", issued on Apr. 1, 2024, with English translation thereof, p. 1-p. 16.
"Office Action of Taiwan Counterpart Application", issued on May 12, 2025, with English translation thereof, pp. 1-12.

* cited by examiner

METHOD FOR PREDICTING PARTICULATE BREAKTHROUGH TIME FOR NON-REGENERATIVE ION EXCHANGE RESIN DEVICE AND METHOD FOR MANAGING NON-REGENERATIVE ION EXCHANGE RESIN DEVICE

CROSS-REFERENCE TO RELATED APPLICATION

This application is a 371 application of the International PCT application serial no. PCT/JP2020/007426, filed on Feb. 25, 2020, which claims the priority benefit of Japan Patent Application No. 2019-149121, filed on Aug. 15, 2019. The entirety of each of the above-mentioned patent applications is hereby incorporated by reference herein and made a part of this specification.

TECHNICAL FIELD

The present invention relates to a method for predicting a particulate breakthrough time of a non-regenerative ion exchange resin device, and a method for managing a non-regenerative ion exchange resin device based on the predicted particulate breakthrough time.

BACKGROUND ART

In the electronic industry field such as liquid crystals and semiconductors for which high-purity pure water and ultra-pure water are required, a non-regenerative ion exchange resin device is often installed in order to remove a very small amount of ions at the end of a primary pure water production device and a secondary pure water production device. As the non-regenerative ion exchange resin device, a mixed bed type ion exchange resin device is often used, but a single-bed type or double-bed type ion exchange resin device is also used.

Since the non-regenerative ion exchange resin device is installed in front of the point of use, if an ion leakage occurs from the non-regenerative ion exchange resin device, there is a risk of an operation of a production facility being stopped. Therefore, in the related art, the non-regenerative ion exchange resin device has been replaced at an early stage, and it has been difficult to use the maximum ion exchange performance of the non-regenerative ion exchange resin device.

As a countermeasure therefor, Patent Literature 1 describes a method in which, since the TOC in primary pure water in front of an ion exchange device in a secondary pure water production device decomposes into carbonic acid in a UV oxidation device, and most of the ion load of the non-regenerative ion exchange device can be considered as carbonic acid, a carbonic acid load amount of the ion exchange device is continuously monitored, and a replacement time for the ion exchange device is predicted from the carbonic acid exchange capacity of the ion exchange device set in advance and the carbonic acid load amount.

In addition, Patent Literature 2 discloses a method in which a compact resin column in which the same ion exchange resin as the ion exchange resin is filled into a column smaller than the column of the non-regenerative ion exchange resin device is installed in parallel to the non-regenerative ion exchange resin device, the same water to be treated as water to be treated that flows through the non-regenerative ion exchange resin device flows through the compact resin column, and an ion breakthrough time of the non-regenerative ion exchange resin device is predicted based on treated water data in the compact resin column.

CITATION LIST

Patent Literature

Patent Literature 1: Japanese Patent Laid-Open No. H11-101761
Patent Literature 2: Japanese Patent Laid-Open No. 2012-154634

SUMMARY OF INVENTION

Technical Problem

However, in each of the methods of predicting a replacement time for a non-regenerative ion exchange resin device described in Patent Literature 1 and Patent Literature 2, the breakthrough time is calculated based on ions from the non-regenerative ion exchange resin device, but since not only ions but also particulates may break through the non-regenerative ion exchange resin device, there is a risk of an operation of the production facility being stopped if particulates leak to the point of use, and there has been no conventional method for predicting a breakthrough time of particulates from a non-regenerative ion exchange resin device.

The present invention has been made in view of the above circumstances and an objective of the present invention is to provide a method for predicting a particulate breakthrough time of a non-regenerative ion exchange resin device and a method for managing a non-regenerative ion exchange resin device provided in a pure water production device based on the particulate breakthrough time predicted by the method.

Solution to Problem

In order to achieve the above objective, primarily, the present invention provides a method for predicting a particulate breakthrough time of a non-regenerative ion exchange resin device in which ion exchange resin is filled into a column, including: measuring the number of particulates in inflow water in the non-regenerative ion exchange resin device; causing water to be treated with a known number of particulates to flow through a compact resin column in which the same ion exchange resin as the ion exchange resin is filled into a column smaller than the column of the non-regenerative ion exchange resin device and measuring the number of particulates in outlet water in the compact resin column; and predicting a particulate breakthrough time of the non-regenerative ion exchange resin device based on the measured number of particulates in the inflow water in the non-regenerative ion exchange resin device and the measured number of particulates in the outlet water in the compact resin column (Invention 1).

According to the invention (Invention 1), when water flows through the compact resin column into which the same ion exchange resin as the ion exchange resin in the non-regenerative ion exchange resin device is filled under conditions in which particulate breakthrough occurs earlier than in the non-regenerative ion exchange resin device, particulate breakthrough occurs in the compact resin column earlier than particulate breakthrough in the non-regenerative ion exchange resin device. Therefore, based on the ratio between filling volumes of the ion exchange resins in the non-regenerative ion exchange resin device and the compact resin column and the difference in water flow conditions between the two, it is possible to predict a particulate breakthrough time of the non-regenerative ion exchange resin device.

In the invention (Invention 1), preferably, the compact resin column is provided in parallel to the non-regenerative ion exchange resin device, and the inflow water in the non-regenerative ion exchange resin device is used as water to be treated in the compact resin column (Invention 2).

According to the invention (Invention 2), it is possible to predict a particulate breakthrough time of the non-regenerative ion exchange resin device in real time according to the change in operation conditions of the non-regenerative ion exchange resin device.

In the invention (Invention 1), the compact resin column through which water to be treated with a known number of particulates flows may be provided independently from the non-regenerative ion exchange resin device (Invention 3).

According to the invention (Invention 3), when the number of particulates in water to be treated that flows through the compact resin column is set to be larger than that of water to be treated in the non-regenerative ion exchange resin device, it is possible to predict a particulate breakthrough time of the non-regenerative ion exchange resin device in a very short time.

In the inventions (Inventions 1 to 3), preferably, an ion exchange resin layer height of the compact resin column is $1/10$ to $3/4$ of an ion exchange resin layer height of the non-regenerative ion exchange resin device (Invention 4). In addition, in the invention (Invention 4), preferably, a diameter of the compact resin column is $1/5$ to $1/40$ of a diameter of the non-regenerative ion exchange resin device (Invention 5).

According to the inventions (Inventions 4 and 5), when the ion exchange resin layer height and the diameter of the compact resin column are set to a predetermined ratio with respect to the non-regenerative ion exchange resin device, since particulate breakthrough in the compact resin column occurs some time before that of the non-regenerative ion exchange resin device, it is possible to appropriately cope with particulate breakthrough in the non-regenerative ion exchange resin device.

In the inventions (Inventions 1 to 5), preferably, water to be treated flows through the compact resin column with a water flow SV that is 1 to 10 times the water flow SV in the non-regenerative ion exchange resin device (Invention 6).

According to the invention (Invention 6), when the water flow SV in the compact resin column is set to a predetermined ratio with respect to the non-regenerative ion exchange resin device, since particulate breakthrough in the compact resin column occurs some time before that of the non-regenerative ion exchange resin device, it is possible to appropriately cope with particulate breakthrough in the non-regenerative ion exchange resin device.

In the inventions (Inventions 1 to 6), preferably, a plurality of the compact resin columns of which at least one of a column diameter, a resin layer height, and a water flow SV differs are disposed (Invention 7).

According to the invention (Invention 7), since a particulate breakthrough time of the non-regenerative ion exchange resin device is predicted based on the particulate breakthrough time of the compact resin columns in which the resin volume of the ion exchange resin and water flow conditions differ, and since prediction results of the particulate breakthrough time of the plurality of non-regenerative ion exchange resin devices are obtained from respective compact resin columns, according to comprehensive determination based on this, the prediction accuracy can be improved.

In the invention (Invention 6), preferably, a time when the number of particulates in outlet water in the compact resin column exceeds a predetermined number is used as a particulate breakthrough point of the compact resin column, and based on a breakthrough time of the compact resin column, a ratio between the water flow SV in the non-regenerative ion exchange resin device and the water flow SV in the compact resin column, and the number of particulates in the inflow water in the non-regenerative ion exchange resin device and the number of particulates in the outlet water in the compact resin column, a particulate breakthrough time of the non-regenerative ion exchange resin device is predicted (Invention 8).

According to the invention (Invention 8), criteria for determining particulate breakthrough in the compact resin column are set as desired conditions, and based on the particulate breakthrough time, it is possible to predict the particulate breakthrough time of the non-regenerative ion exchange resin device at a desired level.

In addition, secondly, the present invention provides a method for managing a non-regenerative ion exchange resin device, including, based on the particulate breakthrough time of the non-regenerative ion exchange resin device predicted by the inventions (Inventions 1 to 8), replacing or maintaining the non-regenerative ion exchange resin device in a pure water production device including the non-regenerative ion exchange resin device (Invention 9).

According to the invention (Invention 9), since a plan for resin replacement or maintenance of the non-regenerative ion exchange resin device is made based on the breakthrough time of the non-regenerative ion exchange resin device predicted according to the breakthrough time of particulates in the compact resin column, it is possible to prevent particulates from leaking from the pure water production device beforehand.

Effects of Invention

According to the present invention, since it is possible to predict a particulate breakthrough time of the non-regenerative ion exchange resin device using the compact resin column into which the same ion exchange resin as the ion exchange resin in the non-regenerative ion exchange resin device is filled, it is possible to prevent particulates from leaking from the pure water production device including the non-regenerative ion exchange resin device beforehand.

DESCRIPTION OF EMBODIMENTS

Hereinafter, a method for predicting a particulate breakthrough time of a non-regenerative ion exchange resin device of the present invention will be described in detail.

First Embodiment

<Ultrapure Water Production Device>

Figure 1:
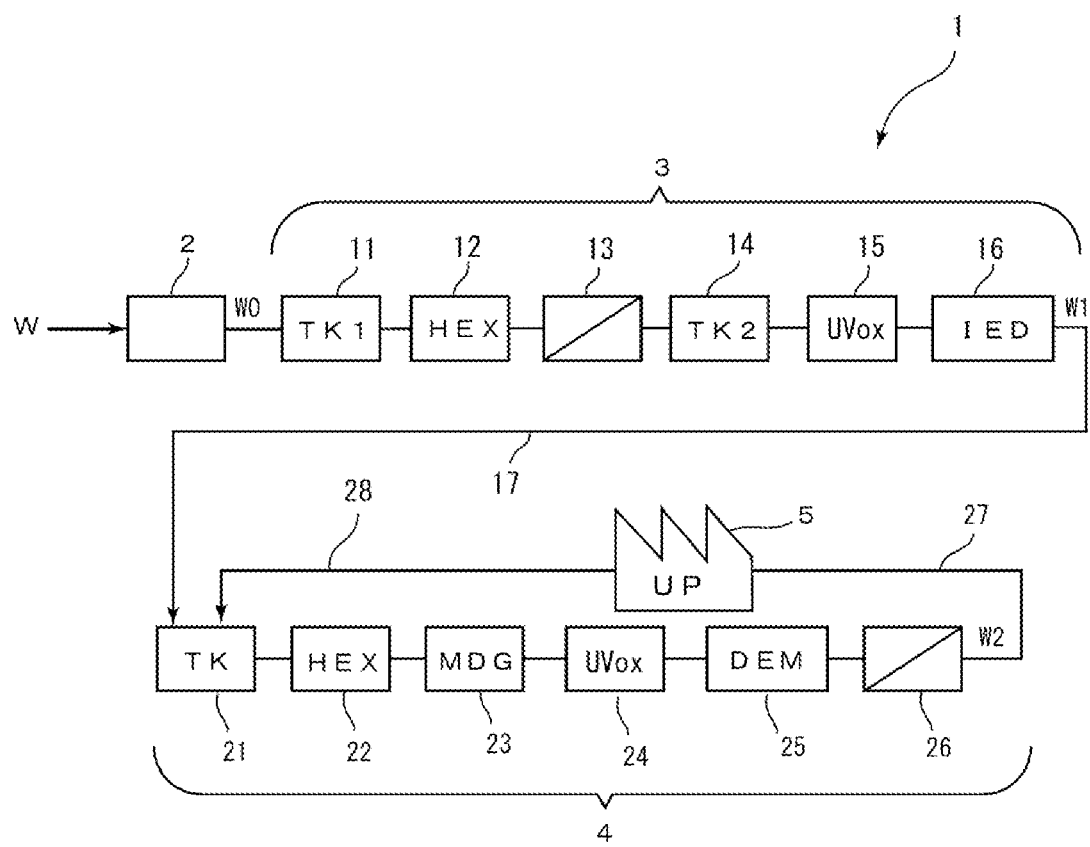
FIG. 1 is a flowchart showing an ultrapure water production device to which a method for predicting a particulate breakthrough time of a non-regenerative ion exchange resin device according to a first embodiment of the present invention can be applied.

FIG. 1 shows an ultrapure water production device to which a method for predicting a particulate breakthrough time of a non-regenerative ion exchange resin device according to the present embodiment can be applied. In FIG. 1, an ultrapure water production device 1 includes a pretreatment system 2, a primary pure water production device 3 and a secondary pure water production device (subsystem) 4 that treats primary pure water and the ultrapure water production device 1 treats raw water industrial water, city water, well water, etc.) W for production.

In the pretreatment system 2 including aggregation, pressure flotation (precipitation), and filter (filtration membrane) devices, suspended substances and colloidal substances in the raw water W are removed. In addition, in this process, it is possible to remove polymer-based organic substances, hydrophobic organic substances, and the like.

A primary pure water production device 3 includes a first tank 11 in which pretreated water W0 is stored, a heat exchanger 12, a reverse osmosis membrane device (RO device) 13, a second tank 14, an UV oxidation device 15 and an ion exchange device (a mixed bed type or a 4-bed 5-tower type, etc.) 16. In the primary pure water production device 3, ions and organic components in raw water are removed. Primary pure water W1 produced by the primary pure water production device is sent to a secondary pure water production device 4 via a pipe 17.

The secondary pure water production device 4 includes a primary pure water tank 21, a heat exchanger 22, a deaeration device 23, a low pressure UV oxidation device (UV oxidizing device) 24, a non-regenerative ion exchange resin device 25 and an ultrafiltration membrane (UF membrane) 26. In the low pressure UV oxidation device 24, TOC is additionally decomposed from organic acids to CO2 with ultraviolet rays of 185 nm emitted from a low pressure UV lamp. Organic substances and CO2 produced by the decomposition are removed in the subsequent non-regenerative ion exchange resin device 25. In the ultrafiltration membrane device 26, particulates are removed, and outflow particles from an ion exchange resin are also removed.

Ultrapure water W2 produced by the secondary pure water production device 4 is sent to a point of use 5 via a pipe 27, and unused ultrapure water is returned to the primary pure water tank 21 via a pipe 28. Here, if the pressure of a pump is insufficient, a boosting pump may be installed (for example, between the UV oxidizing device 24 and the non-regenerative ion exchange resin device 25) upstream from the non-regenerative ion exchange resin device 25.

<Non-Regenerative Ion Exchange Resin Device>

Figure 2:
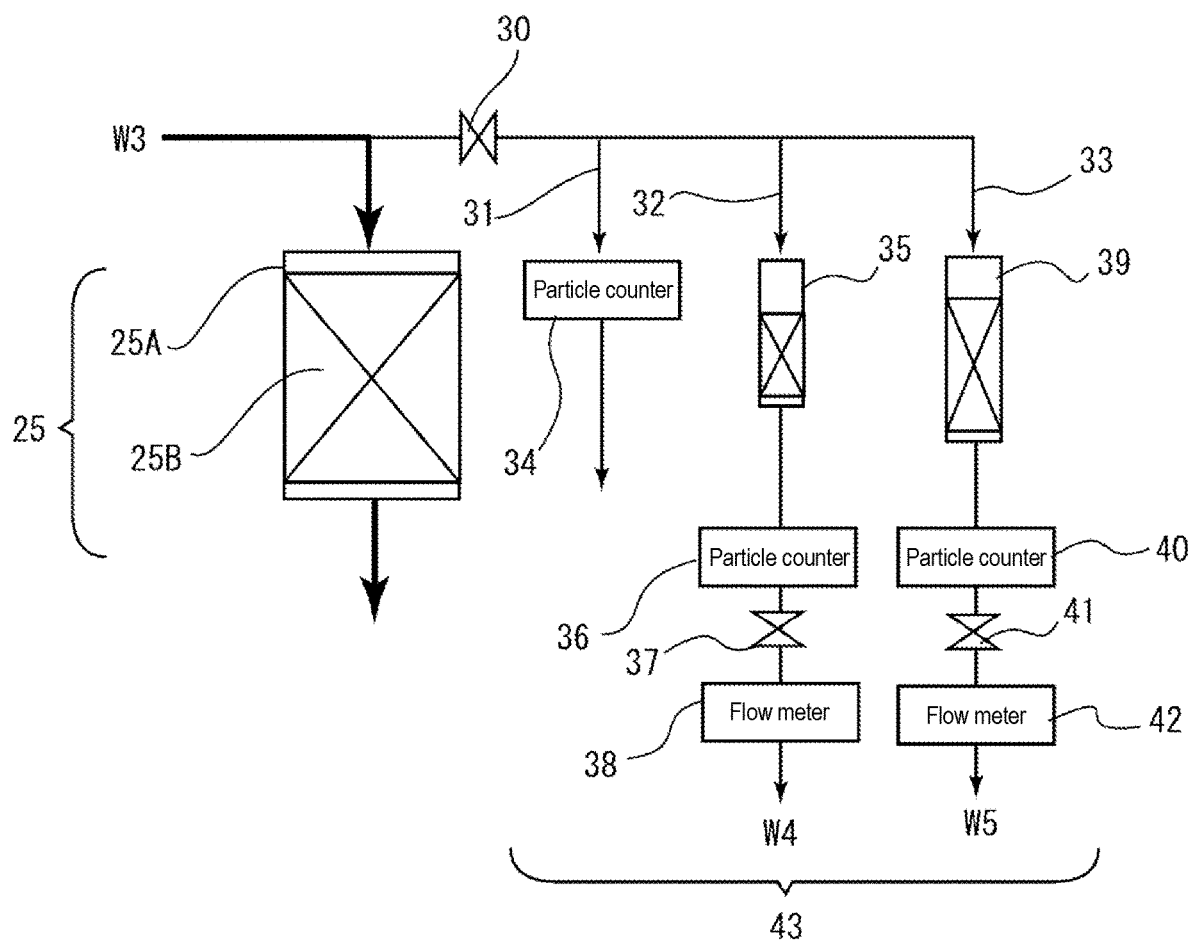
FIG. 2 is a schematic view showing a prediction method using a compact resin column in the same embodiment.

In the ultrapure water production device described above, as shown in FIG. 2, water W3 to be treated flows through the non-regenerative ion exchange resin device 25 and flows out as treated water. The non-regenerative ion exchange resin device 25 includes a column 25A and an ion exchange resin 25B filled into the column 25A.

The non-regenerative ion exchange resin device 25 is installed in the final part of the primary pure water production device or in the secondary pure water production device, and the water quality of the water to be treated is generally at levels of 30 µg/L or less of carbonate ions as C, 1 µg/L or less of chloride ions, 1 µg/L or less of sodium ions, 0.1 µg/L or less of ammonium ions, 10 µg/L or less of boron as B, and 50 µg/L or less of silica as $SiO_2$.

As the non-regenerative ion exchange resin device 25, a mixed bed type ion exchange resin device in which an H type strong cation exchange resin and an OH type strong anion exchange resin are mixed is often used. The mixing ratio of the cation exchange resin and the anion exchange resin in the mixed bed type ion exchange resin device varies depending on the quality of water to be treated, but is preferably cation exchange resin/anion exchange resin=0.2 to 1.0. In a general case, in the present embodiment, the resin layer height in the mixed bed type ion exchange resin device is about 0.3 to 2 m, the column diameter is about 0.3 to 2 m, and the amount of resins is about 0.02 to 6 $m^3$. The water flow SV in the non-regenerative ion exchange resin device is about 30 to 150.

<Compact Resin Column>

Here, a part of water W3 to be treated supplied to the non-regenerative ion exchange resin device 25 flows through a first path 31 including a first particle counter 34 provided in parallel to the non-regenerative ion exchange resin device 25, a second path 32 including a first compact resin column 35, a second particle counter 36, a flow rate regulating valve 37 and a first flow meter 38, and a third path 33 including a second compact resin column 39, a third particle counter 40, a flow rate regulating valve 41 and a second flow meter 42. Here, 30 indicates an on-off valve.

The first compact resin column 35 and the second compact resin column 39 are obtained by filling the same ion exchange resin as the ion exchange resin filled into the non-regenerative ion exchange resin device 25 into a column smaller than the column of the non-regenerative ion exchange resin device 25, and preferably have a cylindrical shape. It is preferable to use the compact resin columns 35 and 39 with both ends in which a mesh having a diameter smaller than the particle size of the resin so that the ion exchange resin does not leak is provided. Here, the compact resin columns 35 and 39 differ in one or more of the column diameter, the resin layer height, and the water flow SV.

The first compact resin column 35 and the second compact resin column 39 preferably have an ion exchange resin layer height of 1/10 to 3/4 of the ion exchange resin layer height of the non-regenerative ion exchange resin device 25. In addition, they have a diameter that is 1/5 to 1/40 of the non-regenerative ion exchange resin device 25, and preferably specifically 20 to 100 mm. When the first compact resin column 35 and the second compact resin column 39 are set to have the above ion exchange resin layer height and diameter, the amount of the ion exchange resin filled in is 0.25 to 15 vol % with respect to the non-regenerative ion exchange resin device 25. If the amount of the ion exchange resin filled in is smaller than 0.25 vol % of the non-regenerative ion exchange resin device 25, the particulate breakthrough time of the first compact resin column 35 and the second compact resin column 39 is too short, and it is difficult to predict the time accurately. On the other hand, if the amount thereof exceeds 15 vol %, the difference in the particulate breakthrough time from the non-regenerative ion exchange resin device 25 becomes small, which is not efficient.

<Method for Predicting Particulate Breakthrough Time>

Next, a method for predicting a particulate breakthrough time of the non-regenerative ion exchange resin device 25 in which the first compact resin column 35 and the second compact resin column 39 described above are arranged side by side will be described.

(Water Flow Method and Water Flow Conditions)

First, while water W3 to be treated flows through the non-regenerative ion exchange resin device 25 at a predetermined flow rate, the same water W3 to be treated flows through the first compact resin column 35 and the second compact resin column 39, and the number of particulates in the treated water (outflow water) W4 and W5 in the compact resin columns 35 and 39 is measured with the second particle counter 36 and the third particle counter 40. On the other hand, the number of particulates (number of inlet particulates) in the water W3 to be treated is measured with the first particle counter 34. It is preferable that the types (organic substances, silica, metals, etc.), physical properties and the like of particulates in the water W3 to be treated be clearly determined in advance by an analysis method such as a centrifugal filtration method. Here, in the present embodiment, the water W3 (W4, W5, etc.) to be treated is sent to a recovery system 43 and reused.

In this case, in the first compact resin column 35 and the second compact resin column 39, it is preferable for water W3 to be treated to flow with a water flow SV that is 1 to 10 times the water flow SV in the non-regenerative ion exchange resin device 25. If the water flow SV is too small, a time taken for particulates to break becomes too long, and it takes a long time to predict the particulate breakthrough time of the non-regenerative ion exchange resin device. On the other hand, when the water flow SV is too large, particulate breakthrough occurs due to a short-term water flow, and thus the prediction accuracy of the particulate breakthrough time deteriorates. Here, SV is [water flow amount]/[filling resin volume]. The first flow meter 38 and the second flow meter 42 measure water flow rates in the first compact resin column 35 and the second compact resin column 39, and the SV may be calculated based on the measured flow rate and the resin filling volume in the first compact resin column 35 and the second compact resin column 39. Then, the flow rates in the first compact resin column 35 and the second compact resin column 39 may be adjusted with the flow rate regulating valve 37, and the flow rate regulating valve 41 so that a desired SV is obtained. Here, the water flow LV is not particularly limited, but it is preferably the same as the water flow LV in the non-regenerative ion exchange resin device 25.

When the water W3 to be treated continuously flows, since the first compact resin column 35 and the second compact resin column 39 have a smaller resin filling amount than the non-regenerative ion exchange resin device 25 and have the same or higher SV, particulate breakthrough occurs in advance with respect to the non-regenerative ion exchange resin device 25. Therefore, if the changes in the number of particulates in the water W3 to be treated and the number of particulates in outflow water in the compact resin columns 35 and 39 over time are measured, and the measured number of particulates in outflow water in the compact resin columns 35 and 39 exceeds a preset numerical value, it is determined that particulate breakthrough has occurred. Then, it is possible to predict a particulate breakthrough time of the non-regenerative ion exchange resin device 25 based on the particulate breakthrough time of the first compact resin column 35 and the second compact resin column 39, the filling ratio of the ion exchange resin in the first compact resin column 35 and the second compact resin column 39 with respect to the non-regenerative ion exchange resin device 25, and the proportion of the water flow SV. Here, it is preferable that the trends of the number of particulates in the compact resin columns 35 and 39 and the number of particulates in the water W3 to be treated be checked constantly with the first particle counter 34, the second particle counter 36 and the third particle counter 40.

(Prediction of Particulate Breakthrough Time)

In the present embodiment, when a time taken for particulates in the compact resin column to breakthrough and a time taken for particulates in the non-regenerative ion exchange resin device to breakthrough are formulated from specifications (the resin layer height, SV, etc.) of the compact resin column, it is possible to predict the particulate breakthrough time in the specifications of the actual non-regenerative ion exchange resin device. For example, based on the relationship between the time taken for particulates in the compact resin column to breakthrough and the SV, formulation is performed by appropriate correction, and the particulate breakthrough time of the non-regenerative ion exchange resin device 25 is calculated in consideration of safety, and this time may be used as a time for replacing and maintaining the non-regenerative ion exchange resin device 25.

Specifically, in the following Formula 1, correction is performed in consideration of the safety ratio according to scale-up (a column diameter, a fluid flow, etc.) of the non-regenerative ion exchange resin device 25 and the compact resin column, and the breakthrough time of the non-regenerative ion exchange resin device 25 may be predicted.

$$\text{Particulate breakthrough time of non-regenerative ion exchange resin device [days]} = \text{Particulate breakthrough time of small column [days]} \times A \times \frac{\text{Water flow } SV \text{ in small column } [1/h]}{\text{Non-regenerative ion exchange}} \quad [\text{Math. 1}]$$

In the formula, A is a correction coefficient in consideration of the scale and safety according to the scale of the compact resin column, and is generally 1 or less. If the value of A is smaller, it is possible to reduce a risk of particulates leaking from the pure water production device (ultrapure water production device) including the non-regenerative ion exchange resin device 25, and on the other hand, if the value of A is larger, it is possible to effectively use the ion exchange resin. Therefore, the value may be set in consideration of the balance between the two. Specifically, the value may be 0.5 to 0.9, and particularly appropriately set to be within a range of 0.6 to 0.8.

Then, in the present embodiment, the particulate breakthrough time of each of the non-regenerative ion exchange resin device 25 in the first compact resin column 35 and the second compact resin column 39 is predicted. For the first compact resin column 35 and the second compact resin column 39, since one or more of a column diameter, a resin layer height, and a water flow SV differ, the particulate breakthrough times differ, and the predicted breakthrough times of the non-regenerative ion exchange resin device 25 generally differ. Therefore, the average value of the two times may be multiplied by the correction coefficient A or a shorter prediction time may be used in consideration of safety and multiplied by the correction coefficient A.

Second Embodiment

Next, a method for predicting a particulate breakthrough time of a non-regenerative ion exchange resin device according to a second embodiment of the present invention will be described.

While the compact resin column is provided in parallel to the non-regenerative ion exchange resin device 25 in the above first embodiment, the present embodiment provides a method in which the compact resin column is provided independently from the non-regenerative ion exchange resin device 25 and an acceleration test is performed.

In the present embodiment, as the ultrapure water production device, the same device as in the above first embodiment can be applied. In addition, as the non-regenerative ion exchange resin device 25 which is a subject of which the particulate breakthrough time is predicted, the same device as in the above first embodiment can be applied. In addition, as the compact resin column, the same column as in the above first embodiment can be used.

<Method for Predicting Particulate Breakthrough Time>

The method for predicting a particulate breakthrough time of the non-regenerative ion exchange resin device 25 according to the second embodiment will be described.

(Water Flow Method and Water Flow Conditions)

First, the number of particulates in water W3 to be treated that flows into the non-regenerative ion exchange resin device 25 is measured in advance. Then, simulated water W6 to be treated containing a larger number of particulates than the number of particulates is prepared. For example, water containing particulates about several tens to several hundred times the number of particulates in water W3 to be treated in the non-regenerative ion exchange resin device 25 is prepared, and thus it is possible to estimate the particulate breakthrough time in a short time in an accelerated manner.

Figure 3:
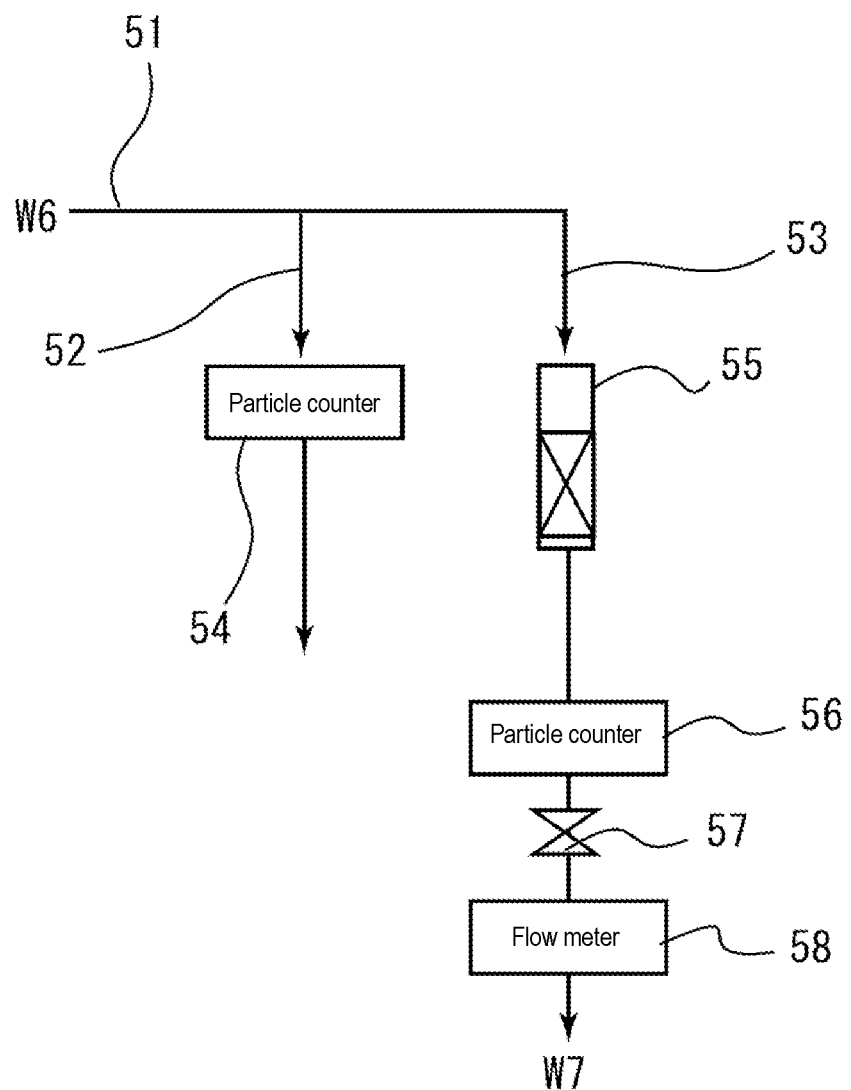
FIG. 3 is a schematic view showing a prediction method using a compact resin column according to a second embodiment of the present invention.

Specifically, as shown in FIG. 3, simulated water W6 to be treated flows from a supply flow path 51 through a first path 52 including a first particle counter 54 and a second path 53 including a compact resin column 55, a second particle counter 56, a flow rate regulating valve 57 and a flow meter 58, and the number of particulates in treated water (outflow water) W7 in the compact resin column 55 is measured with the second particle counter 56. In this case, preferably, simulated water W6 to be treated flows through the compact resin column 55 with a water flow SV that is 1 to 10 times the water flow SV in the non-regenerative ion exchange resin device 25. If the water flow SV is too small, a time taken for particulates to breakthrough becomes too long, and it takes a long time to predict the particulate breakthrough time of the non-regenerative ion exchange resin device. On the other hand, when the water flow SV is too large, particulate breakthrough occurs due to a short-term water flow, and thus the prediction accuracy of the particulate breakthrough time deteriorates. The flow meter 58 measures a water flow rate of the compact resin column 55, and the SV may be measured based on the resin filling volume in the compact resin column 55. Then, the flow rate regulating valve 57 may adjust the flow rate of the compact resin column 55 so that a desired SV is obtained. However, it is desirable to set the water flow SV or the like so that the number of particulates to be processed in the compact resin column 55 is about 10 particulates/ml or less. Here, the water flow LV is not particularly limited, but it is preferable that the water flows LV in the compact resin column 55 and the non-regenerative ion exchange resin device 25 be the same.

When the simulated water W6 to be treated continuously flows, since the compact resin column 55 has a smaller resin filling amount than the non-regenerative ion exchange resin device 25 and the simulated water W6 to be treated has more particulates than the water W3 to be treated, particulate breakthrough occurs in the non-regenerative ion exchange resin device 25 in a very short time. Therefore, when the measured number of particulates in outflow water in the compact resin column 55 exceeds a preset numerical value, it is determined that particulate breakthrough has occurred. Therefore, based on the particulate breakthrough time of the compact resin column 55, the filling ratio of the ion exchange resin in the compact resin column 55 with respect to the non-regenerative ion exchange resin device 25, the proportion of the water flow SV, and the ratio between the numbers of particulates in water W6 to be treated and water W3 to be treated, it is possible to predict a particulate breakthrough time of the non-regenerative ion exchange resin device 25.

(Prediction of Particulate Breakthrough Time)

In the present embodiment, when a time taken for particulates in the compact resin column to breakthrough and a time taken for particulates in the non-regenerative ion exchange resin device to breakthrough are formulated from specifications (the resin layer height, SV, etc.) of the compact resin column, it is possible to predict the particulate breakthrough time in the specifications of the actual non-regenerative ion exchange resin device. For example, based on the time taken for particulates in the compact resin column to breakthrough and the SV, and the ratio relationship between the numbers of particulates in water W6 to be treated and water W3 to be treated, formulation is performed by appropriate correction, the particulate breakthrough time of the non-regenerative ion exchange resin device 25 is calculated in consideration of safety, and this time may be used as a time for replacing and maintaining the non-regenerative ion exchange resin device 25.

Specifically, in the following Formula 2, correction is performed in consideration of the safety ratio according to scale-up (a column diameter, a fluid flow, etc.) of the non-regenerative ion exchange resin device 25 and the compact resin column, and the ratio between the numbers of particulates in water W6 to be treated and water W3 to be treated, and the breakthrough time of the non-regenerative ion exchange resin device 25 may be predicted.

[Math. 2]

$$\text{Particulate breakthrough time of non-regenerative ion exchange resin device [days]} =$$
$$\text{Particulate breakthrough time of small column [days]} \times$$
$$A \times B \times \frac{\text{Number of water supply particulates in small column [number/mL]}}{\text{Number of supply water particulates of non-regenerative ion exchange resin device [number/mL]}} \times$$
$$\frac{\text{Water flow } SV \text{ in small column}}{\text{Water flow } SV \text{ in non-regenerative ion exchange resin device}}$$

In the formula, A is a correction coefficient in consideration of the scale and safety according to the scale of the compact resin column, and is generally 1 or less. If the value of A is smaller, it is possible to reduce a risk of particulates leaking from the pure water production device (ultrapure water production device) including the non-regenerative ion exchange resin device 25, and on the other hand, if the value of A is larger, it is possible to effectively use the ion exchange resin. Therefore, the value may be set in consideration of the balance between the two. Specifically, the value may be 0.5 to 0.9, and particularly appropriately set to be within a range of 0.6 to 0.8. In addition, B is a correction coefficient in consideration of the safety ratio according to an acceleration test in which the number of water supply particulates is changed, and is generally 1 or less. If the value of B is smaller, it is possible to reduce a risk of particulates leaking from the pure water production device (ultrapure water production device) including the non-regenerative ion exchange resin device 25, and on the other hand, if the value of B is larger, it is possible to effectively use the ion exchange resin. Therefore, the value may be set in consideration of the balance between the two. Specifically, the value may be 0.5 to 0.9, and particularly appropriately set to be within a range of 0.6 to 0.8.

While the present invention has been described above based on the above embodiments, the present invention is not limited to the above embodiments, and various modifications can be implemented. For example, in the first embodiment, a plurality of compact resin columns including the first compact resin column 35 and the second compact resin column 39 are provided, one compact resin column may be provided or three or more compact resin columns may be provided in parallel. In addition, in order to accurately estimate the particulate breakthrough time of the non-regenerative ion exchange resin device, it is possible to use a particulate breakthrough prediction simulator or the like.

EXAMPLES

Example 1

In the ultrapure water production device shown in FIG. 1, an acceleration test was performed using one compact resin column in order to predict the breakthrough time of the non-regenerative ion exchange resin device 25.

<Non-Regenerative Ion Exchange Resin Device 25>
Column diameter: 800 mm
Resin layer height: 1,000 mm
Water flow SV: 39/h
Water flow LV: 39 m/h
Number of particulates in water to be treated (water supply): about 100 particulates/mL (>0.05 μm)

<Compact Resin Column>
Column diameter: 40 mm
Resin layer height: 500 mm
Water flow SV: 78/h
Water flow LV: 39 m/h
Number of particulates in simulated water to be treated: about 3,000 particulates/mL (>0.05 μm)

Figure 4:
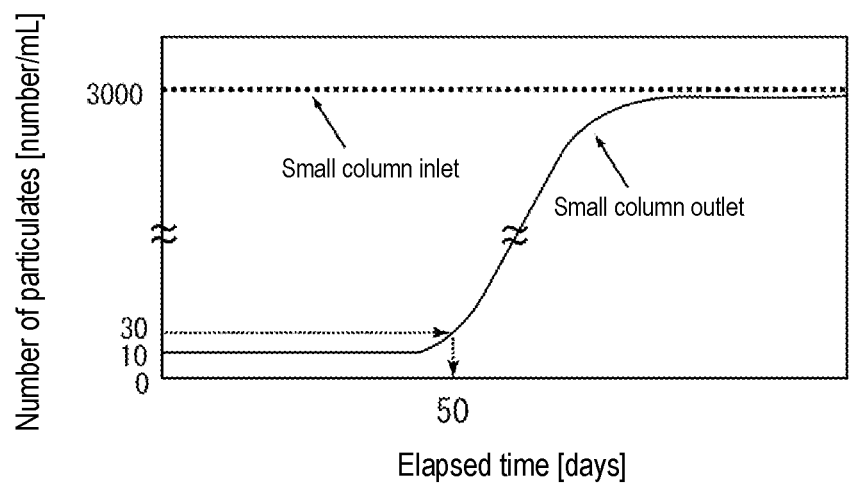
FIG. 4 is a graph showing a particulate breakthrough curve in Example 1.

FIG. 4 shows the results obtained by causing simulated water to be treated to flow in the compact resin column and continuously measuring the number of particulates in the treated water in the compact resin column. Here, when the number of particulates in the treated water was 1% or more of the simulated water to be treated (about 30 particulates/mL (>0.05 μm), if this time was used as a particulate breakthrough point of the compact resin column, as can be clearly understood from FIG. 4, the number of initial particulates was 10 particulates/mL, but exceeded 30 particulates/mL after about 50 days, and thus the $50^{th}$ day was used as the breakthrough point.

Therefore, in the above Formula 2, when the correction coefficients A=0.7 and B=0.7 were set in consideration of the degree of safety, and the particulate breakthrough prediction time of the non-regenerative ion exchange resin device 25 was calculated, the following was calculated:

50 [days]×0.7×0.7×(3,000 [particulates/mL]/100 [particulates/mL])×(78 [l/h]/39 [l/h])=1,470 [days].

Thereby, it can be determined that the non-regenerative ion exchange resin device 25 may be replaced and maintained about 1,500 days after water flow starts as a guide.

REFERENCE SIGNS LIST

25 Non-regenerative ion exchange resin device
31 First path
32 Second path
33 Third path
34 First particle counter
35 First compact resin column
36 Second particle counter
37 Flow rate regulating valve
38 First flow meter
39 Second compact resin column
40 Third particle counter
41 Flow rate regulating valve
42 Second flow meter
51 Supply flow path
52 First path
53 Second path
54 First particle counter
55 Compact resin column
56 Second particle counter
57 Flow rate regulating valve
58 Flow meter
W Raw water
W0 Pretreated water
W1 Primary pure water
W2 Ultrapure water
W3 Water to be treated
W4 Treated water (outflow water) in first compact resin column 35
W5 Treated water (outflow water) in second compact resin column 39
W6 Simulated water to be treated
W7 Treated water (outflow water) in compact resin column 55

What is claimed is:

1. A method for predicting a particulate breakthrough time of a non-regenerative ion exchange resin device in which ion exchange resin is filled into a column, comprising:
measuring the number of particulates in inflow water in the non-regenerative ion exchange resin device;
causing water to be treated with a known number of particulates to flow through a compact resin column in which the same ion exchange resin as the ion exchange resin is filled into a small column smaller than the column of the non-regenerative ion exchange resin device and measuring the number of particulates in outlet water in the compact resin column; and
predicting a particulate breakthrough time of the non-regenerative ion exchange resin device based on the measured number of particulates in the inflow water in the non-regenerative ion exchange resin device and the measured number of particulates in the outlet water in the compact resin column by using the following Formula:

Particulate breakthrough time of non-regenerative ion exchange resin device[days] =

$$\text{Particulate breakthrough time of a small column[days]} \times A \times B \times \frac{\text{Number of water supply particles in small column[number/mL]}}{\text{Number of water supply particles of non-regenerative ion exchange resin device[number/mL]}} \times \frac{\text{Water flow } SV \text{ in small column}}{\text{Water flow } SV \text{ in non-regenerative ion exchange resin device[number/mL]}}.$$

2. The method for predicting a particulate breakthrough time of a non-regenerative ion exchange resin device according to claim 1,
wherein the compact resin column is provided in parallel to the non-regenerative ion exchange resin device, and the inflow water in the non-regenerative ion exchange resin device is used as water to be treated in the compact resin column.

3. The method for predicting a particulate breakthrough time of a non-regenerative ion exchange resin device according to claim 1,
wherein the compact resin column through which water to be treated with a known number of particulates flows is provided independently from the non-regenerative ion exchange resin device.

4. The method for predicting a particulate breakthrough time of a non-regenerative ion exchange resin device according to claim 1,
wherein an ion exchange resin layer height of the compact resin column is 1/10 to 3/4 of an ion exchange resin layer height of the non-regenerative ion exchange resin device.

5. The method for predicting a particulate breakthrough time of a non-regenerative ion exchange resin device according to claim 4,
wherein a diameter of the compact resin column is 1/5 to 1/40 of a diameter of the non-regenerative ion exchange resin device.

6. The method for predicting a particulate breakthrough time of a non-regenerative ion exchange resin device according to claim 1,
wherein water to be treated flows through the compact resin column with the water flow SV that is 1 to 10 times the water flow SV in the non-regenerative ion exchange resin device.

7. The method for predicting a particulate breakthrough time of a non-regenerative ion exchange resin device according to claim 1,
wherein a plurality of the compact resin columns of which at least one of a column diameter, a resin layer height, and a water flow SV differs are disposed.

8. The method for predicting a particulate breakthrough time of a non-regenerative ion exchange resin device according to claim 6,
wherein a time when the number of particulates in outlet water in the compact resin column exceeds a predetermined number is used as a particulate breakthrough point of the compact resin column, and based on a breakthrough time of the compact resin column, a ratio between the water flow SV in the non-regenerative ion exchange resin device and the water flow SV in the compact resin column, and the number of particulates in the inflow water in the non-regenerative ion exchange resin device and the number of particulates in the outlet water in the compact resin column, a particulate breakthrough time of the non-regenerative ion exchange resin device is predicted.

9. A method for managing a non-regenerative ion exchange resin device, comprising:
based on the particulate breakthrough time of the non-regenerative ion exchange resin device predicted by the method for predicting a particulate breakthrough time of a non-regenerative ion exchange resin device according to claim 1, replacing or maintaining the non-regenerative ion exchange resin device in a pure water production device comprising the non-regenerative ion exchange resin device.

* * * * *